United States Patent [19]

Cordier et al.

[11] Patent Number: 5,105,011

[45] Date of Patent: Apr. 14, 1992

[54] PROCESS FOR THE HYDROGENATION OF HALOGENONITRO-AROMATIC COMPOUNDS IN THE PRESENCE OF AN IODIDE

[75] Inventors: Georges Cordier; Jean-Michel Grosselin, both of Francheville, France

[73] Assignee: Rhone-Poulenc Chimie, Courbevoie, France

[21] Appl. No.: 554,514

[22] Filed: Jul. 20, 1990

[30] Foreign Application Priority Data

Jul. 20, 1989 [FR] France .................................. 89 09765

[51] Int. Cl.$^5$ ........................................... C07C 209/36
[52] U.S. Cl. ...................................... 564/417; 502/229
[58] Field of Search ........................ 564/417; 546/311; 502/229

[56] References Cited

U.S. PATENT DOCUMENTS

| | | | |
|---|---|---|---|
| 1,948,330 | 4/1931 | Calvert | 564/417 |
| 3,067,253 | 12/1962 | Dietzler et al. | 564/417 |
| 3,148,217 | 9/1964 | Freyermuth et al. | 564/417 |
| 3,417,090 | 12/1968 | Pelster et al. | 564/417 |
| 4,051,177 | 9/1977 | Braden et al. | 564/422 |

Primary Examiner—Glennon H. Hollrah
Assistant Examiner—Scott C. Rand
Attorney, Agent, or Firm—Finnegan, Henderson, Farabow, Garrett and Dunner

[57] ABSTRACT

A process for the preparation of amino halogeno aromatic compounds, according to which a halogenonitro-aromatic compound is brought into the presence of a nickel-, cobalt- or iron-based catalyst, preferably nickel-based, and, more preferably, Raney nickel, in the presence of an effective amount of iodide, at a temperature and hydrogen pressure sufficient to form said halogenoamino-aromatic compound.

18 Claims, No Drawings

PROCESS FOR THE HYDROGENATION OF HALOGENONITRO-AROMATIC COMPOUNDS IN THE PRESENCE OF AN IODIDE

The present invention relates to a process for the hydrogenation of halogenated aromatic nitro compounds. It relates more particularly to the preparation of halogenated amines.

When carrying out a hydrogenation process on an aromatic nitro compound containing halogen atoms bonded to the aromatic ring, a hydrogenolysis phenomenon of the carbon-halogen bond, to give, on the one hand, the dehalogenated ring and on the other hand, hydrohalic acids, takes place at the same time as the conversion of the nitro group to an amino group. This phenomenon has been known for a very long time and was described in 1904 by P. Sabatier and A. Mailhe.

Numerous patents have been filed which relate to efforts to prevent this side reaction while nonetheless preserving the catalytic activity. These patents can be divided into two groups: those using Raney nickel as the hydrogenation catalyst and those using platinum or palladium. All of these patents describe the use of a modified catalyst.

The Patents U.S. Pat. No. 3,067,253, GB 1,191,610, J 73-49,728, GB 1,498,722 and FR 2,245,615 may be mentioned in the first group of patents which describe the use of Raney nickel.

U.S. Pat. No. 3,067,253 describes the use of Raney nickel to which a calcium hydroxide or magnesium hydroxide has been added. The reaction temperatures reported are nevertheless always low (25° to 60° C.) in order to prevent the dehalogenation, which makes it extremely difficult, if not impossible, to use these processes industrially.

GB Patent 1,191,610 describes the use of Raney nickel in combination with the presence of a thiocyanate. This process at least sometimes involves a relatively slow hydrogenation, and the catalyst is changed during the hydrogenation, which does not allow for continuous processing.

Patent J 73-49,728 describes the use of Raney nickel in combination with the presence of an alkylamine, an alkanolamine or a heterocyclic base. In this patent the hydrogenation temperature is limited, as in the above mentioned U.S. patent, to 60° C., which temperature does not provide satisfactory industrial utilization, since the productivity of the process at such temperature is insufficient. It is also indicated in French Patent 2,245,615 that the process of the Patent J 72-49,728 does not allow the dehalogenation to be prevented in a satisfactory manner since at least 5% of the aniline obtained is dehalogenated.

GB Patent 1,498,722 describes the use of Raney nickel with a trialkyl phosphite. The reaction temperature is reported to be about 100° C., but the degree of dehalogenation varies between 2 and 8%. This process has, therefore, not been thought to be practical on an industrial scale.

The final patent describing the use of Raney nickel is French Patent 2,245,615, which combines Raney nickel with a dehalogenation inhibitor chosen from dicyandiamide, cyanamide and calcium cyanamide. The temperature of the hydrogenation reaction is between 50° and 130° C. and the degree of dehalogenation is stated to be always below 0.15%.

French Patents 2,330,669 and 2,127,092 may be mentioned in the second group of patents describing the use of crude platinum metals. French Patent 2,330,669 describes the use of platinum deposited on charcoal and dehalogenation is inhibited by the presence of a sulfur derivative chosen from the thioethers and the disulfides as the hydrogenation catalyst for chlorinated nitroaromatic compounds. The degree of dehalogenation is reported to be very low (0.01 to 0.08%). This low degree of dehalogenation stems largely from the platinum which, even in the absence of a sulfur derivative, does not cause dehalogenation.

French Patent 2,127,092 describes the preparation of a catalyst of platinum deposited on charcoal which is sulfurized. The preparation of this catalyst consists in first carrying out a hydrogenation of the catalyst and then sulfurizing the latter by the addition of hydrogen sulfide in an amount varying between 0.45 and 0.55 mole of hydrogen sulfide per mole of absorbed hydrogen.

On the one hand the preparation of the catalyst is difficult and, on the other hand, the use of a catalyst deposited on charcoal does not permit easy decanting from the catalytic mass. Thus it is very difficult to use the process in a continuous mode. The use of platinum, a very expensive catalyst, has caused the industry to draw back from the industrial implementation of a process of this type.

The present invention can utilize a nickel-based catalyst, an inexpensive hydrogenation catalyst which settles easily and is therefore particularly well-suited for continuous hydrogenation, as well as cobalt- and iron-based catalysts. The catalyst, such as nickel-based catalyst, can be combined with a dehalogenation inhibitor to impart to the present invention all of the qualities required for the hydrogenation of halogenonitro-aromatic compounds.

The present invention comprises contacting the halogenonitro-aromatic (including polyhalogenonitro-aromatic) compound with (1) a hydrogenation catalyst consisting essentially of a metal selected from nickel, cobalt and iron: (2) an iodide: and (3) at a temperature and hydrogen pressure sufficient to carry out the hydrogenation. The catalyst is preferably nickel-based, and more preferably is Raney nickel. The iodide is preferably chosen from alkali metal iodides or ammonium iodide. It is more preferred to use potassium iodide.

The halogenonitro-aromatic compounds which can be hydrogenated by the process of the present invention to obtain halogenoamino-aromatic compounds correspond to the following formula:

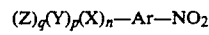

$(Z)_q(Y)_p(X)_n$—Ar—NO$_2$ in which

Ar represents a monocyclic, polycyclic or heterocyclic aromatic radical which may or may not be fused and which may be substituted by an alkyl group containing 1 to 4 carbon atoms, X, Y and Z each independently represents a halogen chosen from fluorine, chlorine and bromine, n, p and q each independently represents an integer of between 0 and 5, the sum n+p+q being equal to or greater than 1 and, preferably, is also less than or equal to 7.

It is preferred to use a monocyclic halogenonitro-aromatic compound containing 1 to 3 halogen atoms, selected from chlorine and fluorine, fixed to the ring, and more preferably the invention utilizes the following compounds:
- chloronitrobenzenes
- fluoronitrobenzenes
- dichloronitrobenzenes
- monochloro-monofluoro-nitrobenzenes
- trichloronitrobenzenes
- chloronitromethylbenzenes
- fluoronitromethylbenzenes The hydrogenation of the halogenonitro-aromatic derivatives with the aid of Raney nickel and the iodide can be carried out under customary hydrogenation conditions. Because of the high non-dehalogenation potential supplied by iodides, it is entirely possible to carry out the hydrogenation at a temperature of from 70° to 150° C. The hydrogenation is preferentially carried out at from 70° to 100° C., which enables productivities (amount of amine formed per hour and per volume of reaction mixture) to be obtained which are advantageously comparable with the productivities of processes aimed at preparing nonhalogenated amines.

Another advantage of the catalyst according to the invention, which was not provided by the catalysts deposited on charcoal, is the ease with which it can be used in processes carried out continuously. In fact, the separation of Raney nickel is clearly easier than that of the catalysts deposited on charcoal.

A final advantage of the catalyst according to the invention is the ease with which it can be used; no prior preparation of the catalyst is necessary, as in French Patent 2,127,092 which requires a hydrogenation of the catalyst followed by its sulfuration. In the present process, it is necessary only to introduce all of the reagents into the hydrogenation reactor (the Raney nickel, the halogenonitro-aromatic compound, the iodide and, if utilized, the solvent) and then to pressurize the reactor with hydrogen.

The process of the invention can be carried out in the absence of solvent or in any solvent which is inert under the reaction conditions, such as, for example:
- water
- alcohols, such as methanol, ethanol or isopropanol and
- aromatic solvents, such as toluene or xylene.

It is preferred to use methanol.

In a preferred embodiment of the invention, it is desirable to use an amount by weight of catalyst, such as Raney nickel, per liter of reaction mixture which is from 1 to 150 g, and preferably from 1 to 5 g, and a molar amount of iodide calculated per liter of reaction mixture of from $10^{-5}$ mole to $10^{-3}$ mole.

When the process is carried out continuously, the amount of halogenonitro-aromatic derivative cannot be established in a static manner. Rather, a continuous process requires addition of this compound in the form of a flow. Thus, flow rates of about 1 to 3 moles per liter of reaction mixture, per hour, are fully recommended.

The hydrogen pressure is advantageously from 1 to 100 bars, preferably 1 to 40 bars, still more preferably from 5 to 25 bars, and most preferably from 20 to 25 bars.

The present invention will be described more completely with reference to the following examples which in no case may be regarded as limiting the invention.

EXAMPLE 1

0.12 g of Raney nickel, x moles of KI (see table below) and 40 ml of 95% methanol were introduced into a 125 ml stainless steel autoclave. After closing, the reactor was purged several times with nitrogen and then with hydrogen.

The pressure was fixed at 20 bars. The reaction mixture was heated to a temperature of 100° C. Once this temperature was reached, 10 g of the substrate (parafluoronitrobenzene/orthofluoronitrobenzene mixture having a molar composition of 90%/10%) were introduced.

At the end of the reaction, the reactor was cooled to ambient temperature and then degassed.

The reaction mixture was filtered through a frit and the filtrate was analyzed by GPC (Gas Phase Chromatography).

The degree of conversion attained was 100%

| KI | % Aniline | ACTIVITY (mole $H_2$/g Ni per h) |
| --- | --- | --- |
| 0 | 2.2 | 1.50 |
| $10^{-5}$M | 1.3 | 1.22 |
| $10^{-4}$M | 0.6 | 1.05 |
| $10^{-3}$M | 0.1 | 0.95 |
| $10^{-2}$M | 0 | 0 |

EXAMPLE 2

Example 1 was repeated, using molar concentration of KI in the reaction mixture of $10^{-3}$M. After settling, the catalyst was recycled 5 times.

| Recycle | % Aniline | ACTIVITY (mole $H_2$/g Ni per h) |
| --- | --- | --- |
| 1 | 0.05 | 0.85 |
| 2 | 0.1 | 0.95 |
| 3 | 0.2 | 0.90 |
| 4 | 0.2 | 0.94 |
| 5 | 0.2 | 0.87 |
| 6 | 0.2 | 0.88 |

What is claimed is:

1. A process for the preparation of a halogenoamino-aromatic compound having at least one halogen selected from the group consisting of fluorine and chlorine bonded to said aromatic ring comprising the step of contacting in the presence or absence of a solvent a halogenonitro-aromatic compound having at least one halogen selected from the group consisting of fluorine and chlorine bonded to said aromatic ring with hydrogen and a catalytic amount of a hydrogenation catalyst consisting essentially of a metal selected from nickel, cobalt, and iron in the presence of an effective amount of iodide, at a temperature and hydrogen pressure sufficient to form said halogenoamino-aromatic compound.

2. A process as claimed in claim 1 wherein the catalyst is nickel.

3. A process as claimed in claim 2 wherein said nickel is Raney nickel.

4. The process as claimed in claim 3, wherein the halogenonitro-aromatic compound corresponds to the formula

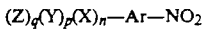

wherein
 Ar represents a monocyclic, polycyclic or heterocyclic aromatic radical which may or may not be fused and which may be substituted by an alkyl group containing 1 to 4 carbon atoms, X, Y and Z each independently represents a halogen selected from fluorine, chlorine and bromine, with the proviso that at least one of X, Y and Z is fluorine or chlorine, n, p and q each independently represents an integer of between 0 and 5, wherein the sum of n+p+q is greater than or equal to 1.

5. The process as claimed in claim 4, wherein Ar represents a monocyclic aromatic radical, and X and Y represent chlorine and/or fluorine and the sum of n+p is greater than or equal to 1 and less than or equal to 3.

6. The process as claimed in claim 1, wherein the iodide is selected from alkali metal iodides and ammonium iodide.

7. The process as claimed in claim 6, wherein the iodide is potassium iodide.

8. The process as claimed in claim 1, wherein the reaction is carried out in the absence of a solvent.

9. The process as claimed in claim 1, wherein said reaction is carried out in the presence of a solvent selected from water, alcohols and aromatic compounds.

10. The process as claimed in claim 9, wherein the solvent is methanol.

11. The process as claimed in claim 1, wherein the amount of hydrogenation catalyst used is from 1 to 150 g per liter of reaction mixture.

12. The process as claimed in claim 11, wherein the amount of hydrogenation catalyst used is from 1 to 5 g per liter of reaction mixture.

13. The process as claimed in claim 1, wherein the molar amount of iodide calculated per liter of reaction mixture is between $10^{-3}$M and $10^{-5}$M.

14. The process as claimed in claim 1, wherein the reaction temperature is from 70° C. to 150° C.

15. The process as claimed in claim 14, wherein said reaction temperature is from 70° C. to 100° C.

16. The process as claimed in claim 1, wherein the hydrogen pressure is from 1 to 100 bars.

17. The process as claimed in claim 16, wherein the hydrogen pressure is from 1 to 40 bars.

18. The process as claimed in claim 17, wherein the hydrogen pressure is from 5 to 25 bars.

* * * * *